United States Patent [19]

Sablotsky

[11] Patent Number: 4,585,452
[45] Date of Patent: Apr. 29, 1986

[54] TRANSDERMAL SYSTEMIC DOSAGE FORMS

[75] Inventor: Steven Sablotsky, Miami, Fla.

[73] Assignee: Key Pharmaceuticals, Inc., Miami, Fla.

[21] Appl. No.: 484,388

[22] Filed: Apr. 12, 1983

[51] Int. Cl.⁴ ............................................. A61M 7/00
[52] U.S. Cl. ................................. 604/896; 604/892; 604/307
[58] Field of Search ............................. 604/896–897, 604/892, 304–308

[56] References Cited

U.S. PATENT DOCUMENTS

| | | | |
|---|---|---|---|
| 2,561,071 | 9/1949 | Prisk | 604/896 |
| 3,797,494 | 4/1974 | Laffaroni | 604/897 |
| 3,964,482 | 6/1976 | Gerstel et al. | 604/896 |
| 4,291,015 | 9/1981 | Keith et al. | 604/896 |
| 4,460,372 | 7/1984 | Campbell et al. | 604/897 |

Primary Examiner—C. Fred Rosenbaum
Assistant Examiner—Sherri E. Vinyard
Attorney, Agent, or Firm—Wegner & Bretschneider

[57] ABSTRACT

Sustained release dosage forms that provide transdermal delivery of drugs utilizing the skin as the rate controlling membrane for the drugs. Methods for producing the dosage forms are also disclosed. The dosage forms are laminates produced by heating a laminate to a glass transition temperature of an outer removable layer of the laminate. While maintaining the laminate at the glass transition temperature, a vacuum is applied to draw the laminate into a suitable shape for a drug reservoir. An aqueous solvent is added to the reservoir and a semipermeable barrier layer is placed over the aqueous solvent in the reservoir. A pharmaceutically active drug is contained in the aqueous reservoir and this drug moves transdermally to provide the active ingredient to the patient.

12 Claims, No Drawings

4,585,452

TRANSDERMAL SYSTEMIC DOSAGE FORMS

BACKGROUND OF THE INVENTION

Transdermal delivery of drugs has become well established in recent years with the introduction of systems such as NITRO-DUR (Key Pharmaceuticals, Inc.), an aqueous polymeric delivery system containing trinitroglycerol. A lactose free system has recently been provided as shown in Key Pharmaceuticals, Inc. PCT application WO No. 83/00093, published Jan. 20, 1983, "Trinitroglycerol Sustained Release Vehicles and Preparations Therefrom." The anti-anginal activity of trinitroglycerol has been well known for many years, and a sustained release of trinitroglycerol through the skin for systemic activity has been known for several decades, as evidenced by Davis et al, Am. J. Med. Sci., 259–263, (Sept. 1955). NITROL (Kremers-Urban) and NITRO-BID (Marion) have been on the market for some time. Gross et al, *Archiv für Toxikologie*, Vol. 18, 194–199, 331–334 (1960), has noted the sustained release of trinitroglycerol in studies that confirm that trinitroglycerol is delivered through the skin at a steady rate. The rate determining step for trinitroglycerol systems is controlled by the skin itself. Around 1970, various sustained release forms were proposed as exemplified by Zaffaroni, U.S. Pat. No. 3,942,751, although none of the embodiments disclosed were put into use. The methods of the early 1970's focused on what has been termed the "biomedical engineering" approach where different layers are bonded together to provide a metering effect through such combination of layers, explained in Robinson, ed., *Sustained and Controlled Release Drug Delivery Systems*, pp. 557–594 (New York: Marcel Dekker, 1978). In the late 1970's, Key Pharmaceuticals, Inc., developed the "chemical" matrix system for the delivery for trinitroglycerol, exemplified by Keith et al, U.S. Pat. No. 4,291,015, and its commercial preparation NITRO-DUR. In such a "chemical" system, delivery rates and other parameters are controlled through the constitution of a matrix with appropriate parameters and do not depend upon layering of other materials as in the "biomedical engineering" approach.

THE INVENTION

Sustained release dosage unit forms are provided that are suitable for transdermal administration of a drug to a patient over a prolonged period of time, where a saturated layer of drug on the skin permits drugs such as trinitroglycerol, propranolol and estrogens to have a delivery rate controlled by the passage of the saturated drug through the skin, as opposed to an external barrier. Any external barrier that would slow the passage of drug to the skin would be extraneous and, to the extent that insufficient drug would reach the skin, a negative effect would result for the purpose of the present invention. In accordance with a first aspect of the present invention there is provided a sustained release dosage unit form suitable for transdermal administration of a drug to a patient over a prolonged period of time wherein the rate control mechanism is based upon saturated drug on the skin whereby the skin is the rate controlling membrane without interference from any barrier to passage of the drug to the skin to defeat said rate control mechanism, which comprises a laminate having a plurality of layers produced by (a) heating a laminate to the glass transition temperature of an outer, removable layer of said laminate, said laminate having
  (i) a siliconized polyvinylidene-chloride-polyvinyl chloride thermoplastic layer to be removed from said dosage unit prior to administration to a patient, said thermoplastic layer having a glass transition temperature sufficiently low so that when said laminate is heated to said glass transition temperature the remaining layers will not be adversely affected;
  (ii) a first adhesive layer of a cross-linked acrylate that is capable of saturation with a high concentration of said drug;
  (iii) a polyurethane semipermeable barrier layer that is both
    (1) permeable to said drug to permit the passage of drug from a reservoir remote from said first adhesive layer without diminishing the rate at which the drug leaves from said first adhesive layer when said adhesive layer becomes saturated with said drug; and
    (2) substantially impermeable to the passage of a solvent from said drug reservoir, said solvent if permitted to substantially enter said first adhesive layer being of a character to impair the adhesive character of said sustained release dosage unit form; and
  (iv) a second adhesive layer on said semipermeable barrier layer remote from said first adhesive layer;
(b) maintaining said laminate at a temperature of at least said glass transition temperature while simultaneously subjecting said thermoplastic layer (i) to a vacuum sufficient to draw said laminate into a well shape suitable as a drug reservoir;
(c) pouring an aqueous solvent containing said drug into the resultant well-shaped reservoir formed in step (b); and
(d) maintaining intimate contact between said aqueous solvent and said semipermeable barrier layer by placing an outer laminate layer over said well-shaped area, said drug migrating over said semi-permeable barrier after production whereby said first adhesive layer is saturated with said drug when said dosage unit is applied to the skin of a patient, said dosage unit form having said thermoplastic layer stripped away prior to applying said first adhesive layer directly to the skin at a site through which said drug is to be transdermally delivered.

The solvent is generally water, but may also include other ingredients such as propylene glycol. It is important to maintain the first adhesive layer substantially free from such solvents, as such solvents may interfere with the drug delivery from the first adhesive layer to the skin. For example, if the first adhesive layer becomes wet, it may be caused to separate from the skin of the patient, thereby defeating the intimate diffusional contact which is necessary for maintaining a saturated drug level at the skin, which in turn is important for sustained release of the drug to the patient, as the skin is the rate controlling membrane in accordance with the present invention. While some drugs such as scopolamine and clonidine may not be suitable for the present invention in that they require a rate controlling membrane, a wide variety of other drugs including trinitroglycerol, propranolol and estrogens pass through the skin at a rate controlled by the skin itself, particularly where a saturated level of the drug is maintained on the skin. It is to be understood that the various forms of drugs that are conventionally used such as esters and pharmaceutically acceptable salts are contemplated within the scope of the present invention. For example, where estradiol is to be transdermally administered, a variety of derivatives, esters and salt forms are contemplated within the scope of the present invention, including ethynylestradiol, estradiol itself, and a variety of estradiol esters, including estradiol benzoate and estradiol acetate.

In a preferred aspect of the present invention, the application of trinitroglycerol is contemplated as a preferred drug, and in this embodiment the trinitroglycerol is contained in said reservoir in a polymeric mixture of from about 2 to about 17% by weight of a first lower molecular weight polyvinylalcohol component having a molecular weight of from about 5,000 to about 40,000; from about 5 to about 22% by weight of a second higher molecular weight, polyvinylalcohol component having a molecular weight of from about 90,000 to about 150,000; and from about 5 to about 15 percent glycerol. While one of the components may be partially hydrolyzed (75 to 92% hydrolysis), in a preferred aspect of the present invention all of the polyvinylalcohol components are fully (about 96-98%) hydrolyzed.

In accordance with a second aspect of the invention, there is provided a sustained release dosage unit form suitable for transdermal administration of a drug to a patient over a prolonged period of time wherein the rate control mechanism is based upon a saturated amount of drug on the skin whereby the skin is the rate controlling membrane without interference from any barrier to passage of the drug to the skin to defeat said rate control mechanism, which comprises a laminate having a plurality of layers which are:

(a) a first adhesive layer having dispersed therein a high concentration of said drug which is based upon an acrylic polymer;

(b) a semipermeable barrier layer which is both
  (i) permeable to said drug to permit the passage of drug from a reservoir remote from said adhesive layer without diminishing the rate at which the drug leaving said adhesive layer passes through the skin of the patient; and
  (ii) substantially impermeable to the passage of a solvent from said drug reservoir, said solvent if permitted to substantially enter said adhesive layer being of a character to impair the adhesive character of said sustained release dosage unit form;

(c) a second adhesive layer;

(d) an aqueous drug reservoir solvent system which contains said drug, said drug providing a supply of said drug to pass through said semipermeable barrier layer into said adhesive layer to replenish the supply of said drug in said adhesive layer as drug from said adhesive layer passes through the skin of the patient; and (e) a backing layer covering said aqueous drug reservoir solvent system and which is adhered to said second adhesive layer around the periphery of said drug reservoir solvent system whereby at the glass transition temperature of the hereinafter mentioned thermoplastic layer the action of a vacuum upon the laminate will permit formation of the well shape without adversely affecting said adhesive layer, said backing layer maintaining said supply of said drug in intimate contact with said semipermeable barrier layer, whereby a high concentration of said drug is contained in said adhesive layer (a) to saturate the skin which is the rate controlling membrane for transdermal delivery of said drug, and whereby drug is permitted to pass freely from said aqueous drug reservoir solvent system (d) through said semipermeable membrane (b) to replenish drug depleted from said adhesive layer (a) and thereby permit the skin to maintain its rate controlling function throughout the prolonged period of administration, said dosage unit form being protected prior to administration to the skin of said patient by a thermoplastic layer on said first adhesive layer. In preferred embodiments, the thermoplastic is a siliconized polyvinylidine chloride-polyvinylchloride and the semipermeable membrane is a polyurethane.

In a third aspect of the present invention there is provided an angina medication in a sustained release dosage unit form suitable for transdermal administration of trinitroglycerol to a patient over a prolonged period of time wherein the rate control mechanism is based upon a saturated amount of trinitroglycerol on the skin whereby the skin is the rate controlling membrane without interference from any barrier to passage of the trinitroglycerol to the skin to defeat said rate control mechanism, which comprises a laminate having a plurality of layers which are produced by (a) heating a laminate to the glass transition temperature of an outer, removable layer of said laminate, said laminate having
  (i) a thermoplastic layer to be removed from said dosage unit prior to administration to a patient, said thermoplastic layer having a glass transition temperature sufficiently low so that when said laminate is heated to said glass transition temperature the remaining layers will not be adversely affected;
  (ii) a first adhesive layer of a material that is capable of saturation with a high concentration of trinitroglycerol;
  (iii) a semipermeable barrier layer that is both
    (1) permeable to said trinitroglycerol to permit the passage of trinitroglycerol from a reservoir remote from said first adhesive layer without diminishing the rate at which the trinitroglycerol leaves from said first adhesive layer when said adhesive layer becomes saturated with said trinitroglycerol; and
    (2) substantially impermeable to the passage of a solvent from said trinitroglycerol reservoir, said solvent if permitted to substantially enter said first adhesive layer being of a character to impair the adhesive character of said sustained release dosage unit form; and
  (iv) a second adhesive layer on said semipermeable barrier layer remote from said first adhesive layer;

(b) maintaining said laminate at a temperature of at least said glass transition temperature while simultaneously subjecting said thermoplastic layer (i) to a vacuum sufficient to draw said laminate into a well shape suitable as a trinitroglycerol reservoir;

(c) pouring into the resultant well-shaped reservoir formed in step (b) trinitroglycerol contained in a polymeric mixture of from about 2 to about 17% by weight of a first lower molecular weight polyvinylalcohol component having a molecular weight of from about 5,000 to about 40,000; from about 5 to about 22% by weight of a second higher molecular weight, polyvinylalcohol component having a molecular weight of from about 90,000 to about 150,000; and from about 5 to about 15 percent glycerol;

(d) maintaining intimate contact between said trinitroglycerol and said semipermeable barrier layer by placing an outer laminate layer over said well-shaped area, said trinitroglycerol migrating over said semipermeable barrier after production whereby said first adhesive layer is saturated with said trinitroglycerol when said dosage unit is applied to the skin of a patient, said dosage unit form having said thermoplastic layer stripped away prior to applying said first adhesive layer directly to the skin at a site through which said trinitroglycerol is to be transdermally delivered.

The thermoplastic layer adjacent to the first adhesive layer is important both in terms of the manufacture of the dosage unit form as well as in terms of protecting the first adhesive layer until just prior to application of the dosage unit form to the skin of the patient. The thermoplastic layer should have a glass transition point that is sufficiently high so that when the dosage unit form is stored at relatively high "normal" temperatures, it will not be caused to deform. At the same time, the glass transition temperature should be sufficiently low so that this layer is capable of being shaped at a temperature not high enough to cause damage to the adhesive. As a thermoplastic material that is contemplated in a preferred aspect of the present invention may be mentioned siliconized polyvinylchloride-polyvinylidine chloride with a glass transition temperature of about 260° F. Shaping of the reservoir is effected by placing the laminate at a ringed structure with a plurality of holes, and removing air from the ringed structure at a vacuum of about 22 inches mercury, whereby a reservoir with a depth of from about 1 to about 2 mm is obtained, into which the solvent system containing the drug is poured. In a preferred embodiment for trinitroglycerol a solvent system containing water, glycerol and propylene glycol is added for the reservoir. The backing layer behind the reservoir is attached to the second adhesive layer, and the backing layer may be, for example, "Saranex".

Trinitroglycerol is preferably present in a substantially disaccharide-free polymeric diffusion matrix for the transdermal systemic delivery of trinitroglycerol through the skin of a patient, said polymeric diffusion matrix containing sufficient trinitroglycerol to be released over a prolonged period of time and which comprises a first lower molecular weight water soluble polymer with hydration sites, a second higher molecular weight water soluble polymer with hydration sites and glycerol. The polymeric diffusion matrix contains by eight from about 2 to about 17%, and more preferably from about 8 to about 15%, of the lower molecular weight, polyvinylalcohol component which may be partially hydrolyzed, but preferably is fully hydrolyzed (i.e., at least about 95%). The lower molecular weight polyvinylalcohol component as used herein is always a generally also fully hydrolyzed form, but optionally may also be partially hydrolyzed with a degree of hydrolysis of about 75 to about 92%, preferably between about 86 and about 90%. As used in all examples herein for a partially hydrolyzed polyvinylalcohol, the degree of hydrolysis is 88%. The lower molecular weight polyvinylalcohol component has a molecular weight of from about 5,000 to about 40,000, and more preferably in the range of from about 10,000 to about 25,000.

There is generally contemplated a range of from about 5 to about 22% of the higher molecular weight water soluble polymer. The higher molecular weight polyvinylalcohol component has a molecular weight of from about 90,000 to about 150,000 and is essentially completely hydrolyzed. The higher molecular weight polyvinylalcohol component generally as at least about 95% hydrolysis and preferably at least about 98% hydrolysis. When used in the examples, the degree of hydrolysis is about 98—99%. As a preferred embodiment may be mentioned a polymer with 115,000 molecular weight and 98% degree of hydrolysis (e.g., Elvanol 90-50, low viscosity grade, DuPont Corporation).

Glycerol is generally present in an amount of from about 5 to about 15 percent, and preferably about 10 percent.

The matrix may include a surface active agent such as alkanolamide, phosphate, sulfate or sulfonate in an amount of from about 0.1 to about 3% by weight, preferably from about 0.5 to about 2% by weight.

The trinitroglycerol is added as a trinitroglycerol/solvent solution. The solvents used include polyethylene glycol, dipropylene glycol, diacetin and acetin. The amount of solvent ranges from about 5% to about 20%. The polymeric mixture includes from about 10 to about 40% lower molecular weight water soluble polymer, for example polyvinylalcohol, and preferably from about 25 to about 30% by weight; from about 2 to about 15% higher molecular weight water soluble polymer, and preferably about 3%; and from about 2 to about 25% glycerol, preferably from about 10 to about 15% by weight. The molecular weight of the lower molecular weight polyvinylalcohol is from about 5,000 to about 40,000, preferably from about 20,000 to about 23,000. The higher molecular weight water soluble polymer component is from about 90,000 to about 150,000, and preferably about 115,000.

In a further variation of the present invention, polyvinylpyrrolidone is contemplated in an amount up to about 2% by weight having a molecular weight from about 20,000 to about 60,000.

The matrix of the invention may also include an alkanolamide in an amount up to about 5%, preferably 0.1 to about 3% by weight. These surface active agents are $C_8$—$C_{18}$ alkanolamides, for example, lauric myristic, lauric, myristic, isostearic, capric, linoleic and combinations thereof. The alkanolamide can be, for examole, Monamid 716 (Mona), Monamid 716P (Mona), Monateric LMAB (Mona), or Monaquat PTL (Mona).

Lactose triturate may be used in the present invention, but it is to be understood that in a preferred aspect a disaccharide-free triturate in a solvent is to be used. It is, of course, essential and very important from the standpoint of safety that sufficiently low concentrations of trinitroglycerol be present to be certain to avoid phase separation. It is to be understood that as a practical matter a maximum of about 20% (and usually only about 10%) trinitroglycerol is included in any of the triturates of the invention. Examples of triturates in the explosives field with higher percentages of nitroglycerin are found in Berthmann et al, British Pat. No. 1,090,184, which discloses methods for manufacture of various triturates. It is to be understood that any pharmacologically acceptable triturate may be prepared, including triturates of the same polymers of Berthmann et al, of course with a much lower concentration of trinitroglycerol than the explosive levels of that patent. As such polymers may be mentioned polymethacrylic acid ester, polyvinyl acetate, ethyl acrylate-vinyl chloride copolymer ("ASTRALON") and polymethyl methacrylate.

It is to be noted that a bandage backing is desirable, but the diffusional contact with the skin is provided by the first adhesive layer. The backing layer may be a simple backing or may be a combination baseplace and facestock with an inert backing material including metal foils and polyesters. The drug containing matrix, in its liquid state, is cast between the above described barrier layer and a coverstrip layer with a double faced adhesive. The barrier coverstrip includes inert materials such as metal foils and polyesters. A label may optionally be included for the rapid identification of drug and dose in emergency situations. Prior to administration the outermost layer, the barrier coverstrip, is pulled away and the matrix in bandage form is affixed to the patient.

As a further embodiment in the packaging of the present matrix, the backing layer may be a conventional backing layer such as is disclosed in Keith et al, U.S. Pat. No. 4,291,015, particularly where the polymeric diffusion matrix is supported through an annular adhesive strip surrounding the polymeric diffusion matrix. The drug-containing diffusion matrix is placed in a cavity provided in an inert backing material. Useful backing materials include metal foils such as aluminum foil, polyolefins such as polyethylene and polypropylene, polyesters such as polyethylene terephthalate, polyamides such as nylon, and the like. The drug-containing diffusion matrix can be poured in its molten state into the cavity and permitted to cool. An adhesive layer is provided on the backing material surrounding the cavity. To prevent evaporative loss in the surface of the matrix, the adhesive layer and the matrix are sealed with a release layer. To use the device, the patient peels off the release layer and places the device in intimate contact with his skin. The exposed adhesive layer secures the device to the patient. A concentration gradient existing normal to the surface of the matrix and the patient's skin facilitates diffusion of the drug through the matrix into the patient's body.

The type of drug which may be used in accordance with the present invention is to be understood to be one which even when saturated on the surface of the skin penetrates the skin in a sufficiently slow manner so that a proper systemic dosage is obtained at that rate. For such a drug, the rate controlling membrane is the skin itself and not a membrane in the laminated structure of the dosage unit form itself. However, the semipermeable barrier, while not impeding the flow of the drug from the reservoir to replenish drug that escapes to the skin from the first adhesive layer, at the same time should be one that blocks the passage of solvents such as water, glycerol and propylene glycol which, if passage were to occur, would adversely affect and loosen the first adhesive layer. The amount of drug that is to be included in the reservoir is not important insofar as sufficient drug is present so that the supply in the first adhesive layer is replenished during the desired prolonged period. While theoretically and occasionally in practice a dosage form for several days may be desired, and this is contemplated within the scope of the present invention, at the same time it is recognized that the dosage of choice in the systemic transdermal field is once every 24 hours, which facilitates better patient compliance. For example, a patient can select a particular time of the day, such as after showering in the morning, or some other fixed and regular event, as the time to replace the dosage form. The location of the dosage form may vary, with the upper chest and the arms as typical locations for application of the dosage form.

Drugs which may be mentioned in addition to trinitroglycerol include propranolol, nicardipine, estrogens, and it is to be specifically contemplated that deriviates, esters and salt forms of the various drugs are to be considered within the scope of the invention. For example, in the case of the estrogens, estradiol is preferably administered in the form of one of the esters, such as the benzoate or valerate, or in the form of a derivative such as the ethynyl derivative. Mixtures of drugs are also contemplated, such as for the estrogen embodiment a mixture of estradiol itself and its benzoate ester. Propranolol is generally used in the form of its hydrochloride and unless otherwise indicated, is to be so used. In addition, isosorbide dinitrate is a further drug that may be advantageously incorporated into the dosage forms of the present invention.

The following examples serve to illustrate the invention:

EXAMPLE I

An aqueous drug reservoir mixture is prepared. Glycerol, at standard 96% concentration, is added to a vessel in an amount to prepare a 10% composition. A first high molecular weight polyvinylalcohol component (mw 90,000, fully hydrolyzed; Elvanol 90-50, DuPont) is added to yield 10% of the final product. The second polyvinylalcohol component which is added is of a molecular weight of 22,000 and also fully hydrolyzed (Vinol 107), which is added in an amount to yield a final percentage composition of 12%. Sufficient deionized water is added to so that, together with the trinitroglycerol mixture to be added later, the total ingredients make up 100%. After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture. Added to this mixture is a trinitroglycerol solution to make up 20% of the total mixture, this trinitroglycerol solution itself containing 10% trinitroglycerol and 90% propylene glycol, i.e., the total final weight of trinitroglycerol in the reservoir mixture is 2% and propylene glycol is 18%. Preparation of this trinitroglycerol solution may be accomplished by adding lactose triturate (10% trinitroglycerol) to sufficient acetone to put the trinitroglycerol in solution, after which the acetone solution is admixed with propylene glycol in an amount sufficient to yield an eventual trinitroglycerol concentration in a solution thereof of 10% (exclusive of the weight of the acetone). The lactose is then separated from the solution. The resultant solution is thereafter treated to heating under vacuum to yield the acetone-free trinitroglycerol solvent mixture which is then poured into the drug reservoir polymer mixture.

The drug-containing polymer mixture is then poured into a well-shaped area formed on a second adhesive layer of a laminate film having first and second adhesive layers on a polyurethane semipermeable barrier layer, the first layer being covered with a polyvinylidene chloride-polyvinylchloride backing layer having a glass transition temperature of about 260° F. (This layer is generally a thermoplastic material that, as contemplated in a preferred aspect of the present invention, may be as previously mentioned, siliconized polyvinylchloride-polyvinylidine chloride with a glass transition temperature of about 260° F.) The adhesive is a cross-linked acrylic adhesive which is both highly adherent to the surface of the skin and which also draws a high concentration of drug through the semipermeable barrier of polyurethane. The well-shaped area having a depth of about 1.5 mm and a diameter of about 3.6 cm is itself created by contacting the polyvinylidene chloride-polyvinylchloride layer of the laminate to a ringed structure of the appropriate diameter and depth to form the well-shaped area, whch is supplied with means to create a vacuum in the form of a plurality of holes in the well area, air being withdrawn from these holes at a pressure of 22 inches mercury to thereby suck the laminate into the well shaped mold. Prior to application of this pressure, the laminate is heated to a temperature too low to adversely affect the adhesive but high enough to reach the glass transition temperature, which in a preferred embodiment is 260° F.; the temperature is maintained at this level during the vacuum process, after which the laminate is permitted to cool to room temperature.

After the drug mixture has been poured into the well shaped area over the second adhesive layer, a backing layer is attached thereover which may be made of any conventional backing layers, for example, "Saranex." This backing layer forms an annular seal securing the entire dosage form, tightly sealing the drug reservoir in place over the polyurethane layer through the annular ring of the second adhesive layer surrounding the reservoir area.

When placed on the skin of a subject, a sustained release for a period of at least 24 hours, and often much longer, is achieved, due to the release kinetics which depend upon the skin as the rate controlling barrier, neither the first adhesive layer nor the polyurethane preventing a continued saturated condition of the drug at the skin layer.

EXAMPLE II

An aqueous drug reservoir mixture is prepared. Glycerol, at standard 96% concentration, is added to a vessel in an amount to prepare a 10% composition. A first high molecular weight polyvinylalcohol component (mw 115,,000, fully hydrolyzed, as used in Example I of Keith et al, U.S. Pat. No. 4,291,015, granted Sept. 22, 1981) is added to yield 8% of the final product. The second polyvinylalcohol component which is added is of a molecular weight of 15,000 and also fully hydrolyzed, which is added in an amount to yield a final percentage composition of 15%. Sufficient deionized water is added to so that, together with the trinitroglycerol mixture to be added later, the total ingredients make up 100%. After each of the mentioned components has been added to the vessel, whch typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture. Added to this mixture is a trinitroglycerol solution to make up 20% of the total mixture, this trinitroglycerol solution itself containing 10% trinitroglycerol and 90% propylene glycol, i.e., the total final weight of trinitroglycerol in the reservoir mixture is 2% and propylene glycol is 18%. A trinitroglycerol dosage form is thereafter prepared by following the remaining procedures as set forth in Example I.

EXAMPLE III

The procedure of Example I is repeated exactly, except that the following variation is used in the preparation of the aqueous drug reservoir mixture. In Example I, there is used glycerol, at standard 96% concentration, which added to a vessel in an amount to prepare a 10% compositiion. Instead, sufficient glycerol to make up 5% of the total amount, with additional water to compensate for the lesser amount of glycerol is used.

EXAMPLE IV

Propranol (in the form of its hydrochloride) is included in an aqueous drug reservoir mixture. A first high molecular weight polyvinylalcohol component (mw 90,000, fully hydrolyzed; Elvanol 90–50, DuPont) is added to yield 10% of the final product to a vessel which already contains sufficient glycerol, at standard 96% concentration to prepare a final composition containing 10% glycerol. The second polyvinylalcohol component which is added is of a molecular weight of 22,000 and also fully hydrolyzed (Vinol 107), which is added in an amount to yield a final percentage composition of 12%. Sufficient deionized water is added to so that, together with the trinitroglycerol mixture to be added later, the total ingredients make up 100%. After each of the mentioned components has been added to the vessel, which typically may be a beaker for experimental studies, the components are thoroughly mixed. The resultant mixture is placed in a microwave oven and heated to the boiling point. 2 gm propranolol is then incorporated into this mixture, and the beaker is then covered and thereafter transferred to a steam bath and the process continued until full extension of the polymers contained in the mixture. The drug-containing polymer mixture is then poured into a well-shaped area formed on a second adhesive layer of a laminate film having first and second adhesive layers on a polyurethane semipermeable barrier layer, the first layer being covered with a polyvinylidene chloride-polyvinylchloride backing layer having a glass transition temperature of about 260° F. (This layer is generally a thermoplastic material that is contemplated in a preferred aspect of the present invention may be mentioned siliconized polyvinylchloride-polyvinylidine chloride with a glass transition temperature of about 260° F.) The adhesive is a cross-linked acrylic adhesive which is both highly adherent to the surface of the skin and which also draws a high concentration of drug through the semipermeable barrier of polyurethane. The well-shaped area having a depth of about 1.5 mm and a diameter of about 3.6 cm is itself created by contacting the polyvinylidene chloride-polyvinylchloride layer of the laminate to a ringed structure of the approrpriate diameter and depth to form the well-shaped area, which is supplied with means to create a vacuum in the form of a plurality of holes in the well area, air being withdrawn from these holes at a pressure of 22 inches mercury to thereby suck the laminate into the well shaped mold. Prior to application of this pressure, the laminate is heated to a temperature too low to adversely affect the adhesive but high enough to reach the glass transition temperature, which in a preferred embodiment is 260° F.; the temperature is maintained at this level during the vacuum process, after which the laminate is permitted to cool to room temperature. After the drug mixture has been poured into the well shaped area over the second adhesive layer, a backing layer is attached thereover which may be made of any conventional backing layers, for example, "Saranex." This backing layer forms an annular seal securing the entire dosage form, tightly sealing the drug reservoir in place over the polyurethane layer through the annular ring of the second adhesive layer surrounding the reservoir area.

When placed on the skin of a subject, a sustained relesae for a period of at least 24 hours, and often much longer, is achieved, due to the release kinetics which depend upon the skin as the rate controlling barrier, neither the first adhesive layer nor the polyurethane preventing a continued saturated condition of the drug at the skin layer.

EXAMPLE V

Estrogens are included in an aqueous drug reservoir mixture. A first high molecular weight polyvinylalcohol component (mw 90,000, fully hydrolyzed; Elvanol 90-50, DuPont) is added to yield 10% of the final product to a vessel which already contains sufficient glycerol, at standard 96% concentration to prepare a final composition containing 10% glycerol. The second polyvinylalcohol component which is added is of a molecular weight of 22,000 and also fully hydrolyzed (Vinol 107), which is added in an amount to yield a final percentage composition of 12%. Sufficient deionized water is added to so that, together with the trinitroglycerol mixture to be added later, the total jngredients make up 100%. After each of the mentioned components has been added to the vessel which typically may be a beaker for experimental studies, the components are thoroughly mixed. The resultant mixture is placed in a microwave oven and heated to the boiling point. 1 gm estradiol and 1 gm estradiol benzoate are mixed together, and this estrogen mixture is then incorporated into this mixture, and the beaker is then covered and thereafter transferred to a steam bath and the process continued until full extension of the polymers contained in the mixture. The drug-containing polymer mixture is then poured into a well-shaped area formed on a second adhesive layer of a laminate film having first and second adhesive layers on a polyurethane semipermeable barrier layer, the first layer being covered with a polyvinylidene chloride-polyvinylchloride backing layer having a glass transition temperature of about 260° F. (This layer is generally a thermoplastic material that is contemplated in a preferred aspect of the present invention may be mentioned siliconized polyvinylchloride-polyvinylidine chloride with a glass transition temperature of about 260° F.) The adhesive is a cross-linked acrylic adhesive which is both highly adherent to the surface of the skin and which also draws a high concentration of drug through the semipermeable barrier of polyurethane. The well-shaped area having a depth of about 1.5 mm and a diameter of about 3.6 cm is itself created by contacting the polyvinylidene chloride-polyvinylchloride layer of the laminate to a ringed structure of the appropriate diameter and depth to form the well-shaped area, which is supplied with means to create a vacuum in the form of a plurality of holes in the well area, air being withdrawn from these holes at a pressure of 22 inches mercury to thereby suck the laminate into the well shaped mold. Prior to application of this pressure, the laminate is heated to a temperature too low to adversely affect the adhesive but high enough to reach the glass transition temperature, which in a preferred embodiment is 260° F.; the temperature is maintained at this level during the vacuum process, after which the laminate is permitted to cool to room temperature. After the drug mixture has been poured into the well shaped area over the second adhesive layer, a backing layer is attached thereover which may be made of any conventional backing layers, for example, "Saranex". This backing layer forms an annular seal securing the entire dosage form, tightly sealing the drug reservoir in place over the polyurethane layer through the annular ring of the second adhesive layer surrounding the reservoir area.

When placed on the skin of a subject, a sustained relesae for a period of at least 24 hours, and often much longer, is achieved, due to the release kinetics which depend upon the skin as the rate controlling barrier, neither the first adhesive layer nor the polyurethane preventing a continued saturated condition of the drug at the skin.

EXAMPLE VII

Instead of the 2 gm estrogen mixture used in Example VI, ethynylestradiol is substituted in a like amount. Estradiol valerate and other estradiol esters may also be used in the matrix of Example VI to provide an increased effective dosage.

EXAMPLE VIII

Instead of the trinitroglycerol solution of Example I, sufficient isosorbide dinitrate is added to make up 4% of the final polymer mixture, to produce a transdermal dosage system to deliver nitrate to a patient.

EXAMPLE IX

Instead of the trinitroglycerol solution of Example I, 5 gm nicardipine is added to the polymer mixture, to produce a transdermal dosage system.

What is claimed is:

1. A sustained release dosage unit form suitable for transdermal administration of a drug to a patient over a prolonged period of time wherein the rate control mechanism is based upon a saturated amount of drug on the skin of said patient and said skin is the rate controlling membrane without interference from any barrier to passage of said drug to said skin to defeat said rate control mechanism, said sustained release dosage unit form comprising a laminate produced by (a) providing a laminate having
  (i) an outer, removable layer comprising a siliconized polyvinylidine chloride-polyvinyl chloride thermoplastic layer that can be removed from said laminate prior to administration of said sustained release dosage unit form to said patient, said thermoplastic layer having a glass transition temperature sufficiently low so that, upon heating of said laminate to said glass transition temperature, the remaining layers of said laminate will not be effected adversely;
  (ii) a first adhesive layer of a cross-linked acrylate polymer that is capable of saturation with said drug;
  (iii) a polyurethane semipermeable barrier layer that is both
    (1) permeable to said drug to permit passage of said drug from a reservoir remote from said first adhesive layer (ii) without diminishing the rate at which said drug leaves said first adhesive layer when it is saturated with said drug; and (2) substantially impermeable to passage of a solvent from said drug reservoir, said solvent, if permitted substantially to enter said first adhesive layer being of a character to impair the adhesive character of said sustained release dosage unit form; and (iv) a second adhesive layer on said semipermeable barrier layer (iii) remote from said first adhesive layer (ii);

(b) heating said laminate to at least the glass transition temperature of said outer, removable layer;

(c) maintaining the heated laminate of step (b) at a temperature of at least said glass transition temperature while simultaneously subjecting said outer, removable layer (i) to a vacuum sufficient to draw said laminate into a well shape to function as a drug reservoir;

(d) pouring an aqueous solvent containing said drug into the well-shaped drug reservoir formed in step (c); and (e) maintaining intimate contact between said aqueous solvent and said semipermeable barrier layer (iii) by placing an outer laminate layer (v) over said well-shaped area, wherein said drug migrates over said semipermeable barrier layer (iii) after production of said sustained release dosage unit form causing said first adhesive layer (ii) to be saturaed with said drug when said sustained release dosage unit form is applied to said skin of said patient, said sustained release dosage unit form having said outer, removable layer (i) stripped away from said sustained release dosage unit form prior to applying said first adhesive layer (ii) directly to said skin at a site through which said drug is to be transdermally delivered.

2. A sustained release dosage unit form of claim 2 wherein said solvent is water.

3. A sustained release dosage unit form of claim 2 wherein said solvent includes propylene glycol.

4. A sustained release dosage unit form of claim 3 wherein said drug is trinitroglycerol contained in said reservoir in a polymeric mixture of from about 2 to about 17% by weight of a first lower molecular weight polyvinylalcohol component having a molecular weight of from about 5,000 to about 40,000; from about 5 to about 22% by weight of a second higher molecular weight, polyvinylalcohol component having a molecular weight of from about 90,000 to about 150,000; and from about 5 to about 15 percent glycerol.

5. A sustained release dosage form of chain 4 wherein the polyvinylalcohol components are fully hydrolyzed.

6. A sustained release dosage form of claim 1 wherein said drug is propranolol.

7. A sustained release dosage form of claim 1 wherein said drug is an estrogen.

8. A sustained release dosage form of claim 7 wherein said estrogen includes at least one estradiol ester.

9. A sustained release dosage form of claim 8 wherein said estradiol ester is estradiol benzoate.

10. An angina medication in a sustained release dosage unit form suitable for transdermal administration of trinitroglycerol to a patient over a prolonged period of time wherein the rate control mechanism is based upon a saturated amount of trinitroglycerol on the skin of said patient and said skin is the rate controlling membrane without interference from any barrier to passage of trinitroglycerol to said skin to defeat said rate control mechanism, said sustained release dosage unit form comprising a laminate produced by (a) providing a laminate having (i) an outer, removable layer comprising a siliconized polyvinylidene chloride-polyvinyl chloride thermoplastic layer that can be removed from said laminate prior to administration of said sustained release dosage unit form to said patient, said thermoplastic layer having a glass transition temperature sufficiently low so that, upon heating of said laminate to said glass transition temperature, the remaining layers of said laminate will not be affected adversely;

(ii) a first adhesive layer of material that is capable of saturation with trinitroglycerol;

(iii) a semipermeable barrier layer that is both (1) permeable to trinitroglycerol to permit passage of trinitroglycerol from a reservoir remote from said first adhesive layer (ii) without diminishing the rate at which trinitroglycerol leaves said first adhesive layer when it is saturated with trinitroglycerol; and (2) substantially impermeable to passage of a solvent from said reservoir, said solvent, if permitted substantially to enter said first adhesive layer being of a character to impair the adhesive character of said sustained release dosage unit form; and (iv) a second adhesive layer on said semipermeable barrier layer (iii) remote from said first adhesive layer (ii);

(b) heating said laminate to at least the glass transition temperature of said outer , removable layer;

(c) maintaining the heated laminate of step (b) at a temperature of at least said glass transition temperature while simultaneously subjecting said outer, removable layer (i) to a vacuum sufficient to draw said laminate into a well shape to function as a trinitroglycerol reservoir;

(d) pouring into the well-shaped trinitroglycerol reservoir formed in step (c) trinitroglycerol contained in a polymeric mixture of from about 2 to about 17% by weight of a first lower molecular weight polyvinylalcohol component having a molecular weight of from about 5,000 to about 40,000; from about 5 to about 22% by weight of a second higher molecular weight polyvinylalcohol component having a molecular weight of from about 90,000 to about 150,000; and from about 5 to about 15 percent glycerol; and (e) maintaining intimate contact between said trinitroglycerol and said semipermeable barrier layer (iii) by placing an outerlaminate layer (v) over said well-shaped area, wherein trinitroglycerol migrates over said semipermeable barrier layer (iii) after production of said sustained release dosage unit form causing said first adhesive layer (ii) to be saturated with trinitroglycerol when said sustained release dosage unit form is applied to said skin of said patient, said sustained release dosage unit form having said outer, removable layer (1) stripped away from said sustained release dosage unit form prior to applying said first adhesive layer (ii) directly to said skin at a site through which trinitroglycerol is to be transdermally delivered.

11. A sustained release dosage form of claim 11 wherein the polyvinylalcohol components are fully hydrolyzed.

12. A sustained release dosage form of claim 11 wherein the semipermeable membrane is a polyurethane.

* * * * *